United States Patent
Kurth (12)

(10) Patent No.: US 6,219,408 B1
(45) Date of Patent: Apr. 17, 2001

(54) APPARATUS AND METHOD FOR SIMULTANEOUSLY TRANSMITTING BIOMEDICAL DATA AND HUMAN VOICE OVER CONVENTIONAL TELEPHONE LINES

(76) Inventor: Paul Kurth, 30423 Miraleste Dr., Rancho Palos Verdes, CA (US) 90275

( * ) Notice: Subject to any disclaimer, the term of this patent is extended or adjusted under 35 U.S.C. 154(b) by 0 days.

(21) Appl. No.: 09/322,213

(22) Filed: May 28, 1999

(51) Int. Cl.$^7$ .................................................. H04M 11/00
(52) U.S. Cl. ................................. 379/106.02; 379/110.01
(58) Field of Search .......................... 379/106.01, 106.02, 379/110.01, 90.01, 93.05, 93.06, 93.08, 93.28, 440–446; 381/67

(56) References Cited

U.S. PATENT DOCUMENTS

| | | |
|---|---|---|
| 3,872,252 | 3/1975 | Malchman et al. . |
| 3,882,277 | 5/1975 | DePedro et al. . |
| 4,151,513 * | 4/1979 | Menken et al. ................... 379/106.02 |
| 4,608,987 | 9/1986 | Mills . |
| 5,321,618 | 6/1994 | Gessman . |
| 5,343,869 | 9/1994 | Pross et al. . |
| 5,474,090 | 12/1995 | Begun et al. . |
| 5,522,396 | 6/1996 | Langer et al. . |
| 5,634,468 | 6/1997 | Platt et al. . |
| 5,678,562 | 10/1997 | Sellers . |
| 5,694,940 | 12/1997 | Unger et al. . |
| 5,704,351 | 1/1998 | Mortara et al. . |
| 5,704,364 | 1/1998 | Saltzstein et al. . |
| 5,730,146 | 3/1998 | Itil et al. . |

\* cited by examiner

Primary Examiner—Wing F. Chan
(74) Attorney, Agent, or Firm—Daniel L. Dawes, Esq.; Myers, Dawes & Andras LLP

(57) ABSTRACT

The present invention is an apparatus for simultaneously transmitting biomedical signals and human voice over a telephone. The invention is also a telephone line adapted to receive communication from the receiving unit at a second end of the line while simultaneously transmitting biomedical signals and human voice from the first end. The apparatus comprises a sensor, a cable, and a transmitter device. The sensor comprises electrodes attached to a pad with a wire connected to each electrode. The cable groups the wires into a single unit and leads them to the transmitter device. The transmitter device comprises a converter and a acoustic. In operation, the sensor takes biomedical signals in the form of electronic data. The data is conveyed via the wires where it reaches the converter. The converter converts the biomedical electronic data into acoustic signal which is emitted by the acoustic in circuit with the converter. The acoustic signals are translatable back to biomedical signals by the receiving unit. The acoustic is disposed within acoustic range of the microphone of a telephone. The acoustic is disposed in such a manner as to allow oral speech from the patient to be transmitted simultaneously with the transmission of the sound. The invention may also comprise its own telephone member which may then be plugged into an conventional telephone base.

23 Claims, 5 Drawing Sheets

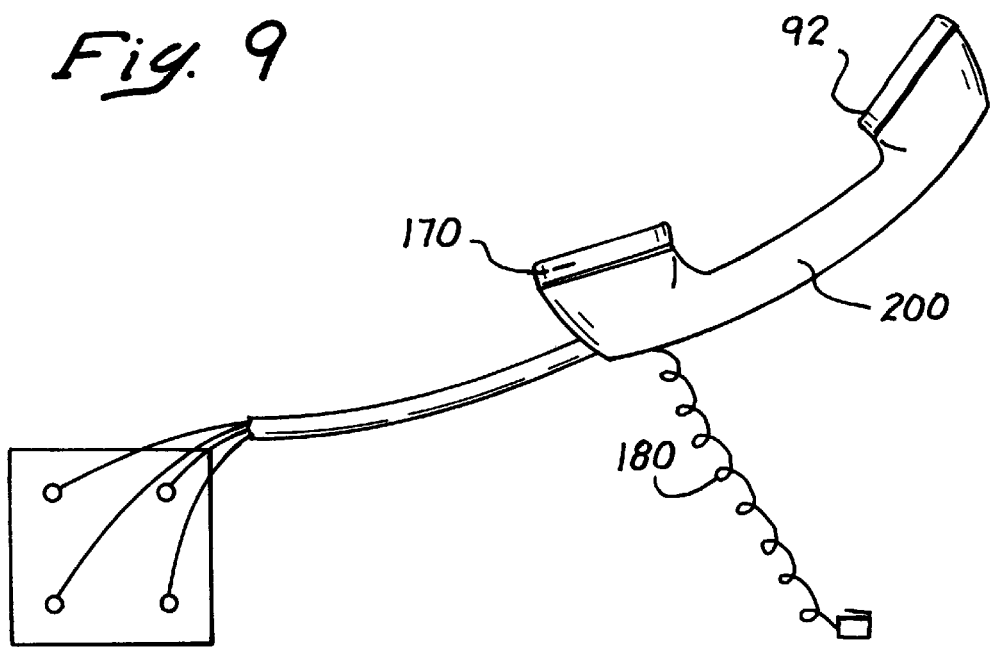
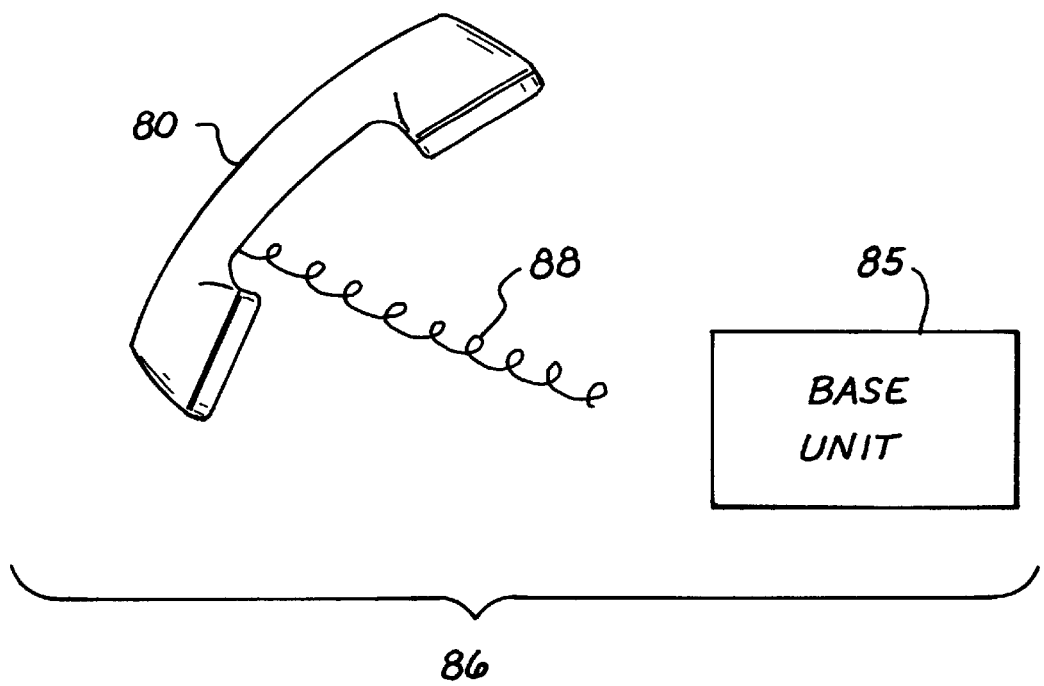

APPARATUS AND METHOD FOR SIMULTANEOUSLY TRANSMITTING BIOMEDICAL DATA AND HUMAN VOICE OVER CONVENTIONAL TELEPHONE LINES

BACKGROUND OF THE INVENTION

1. Field of the Invention

The invention relates to devices used for reading and transmitting biomedical data over the telephone.

2. Description of Prior Art

Patients with specific health conditions may require constant supervision and examination by their physicians or health technicians. However, getting oneself to a hospital or clinic may be impossible, impractical or inconvenient. In addition the use of remote monitoring of the patient by the health care provider is becoming increasingly more common. The remote monitoring of EKG signals has been practice for many years. The prior art includes biomedical devices that allow a patient to perform biomedical readings upon himself or herself and transmit these readings over the telephone.

In conducting these self-readings, it is often important to apply the reader or sensor in the proper place and in the proper manner. The conventional remote monitoring EKG device is comprised of a plurality of skin electrodes that are wired into a transmitter box which has an acoustic coupler provided in its top surface. The handset of the phone through which the EKG signals are being transmitted to a receiving unit at the hospital or physician's office is placed into a receiver cradle on the top of the transmitter box. In the conventional acoustic coupling device, the patient and the technician cannot speak to or hear each other during the interval in which the reading occurs, because the handset is intimately coupled to the acoustic coupler on the top of the transmitter box. A slight misconfiguration or bodily movement after a proper configuration may upset the readings and render the results useless.

In such a case, the patient must make and transmit the reading over again. Typically, what occurs is that the initial few electrode placements are faulty and the receiving technician attempts to get the patient's attention by shouting over the phone in the hope of being heard from the phone's earpiece lying on top of the acoustic coupler. Eventually, the patient realizes that the placements are faulty either by hearing the technician's loud yelling, or by speaking to the technician after a faulty test has been completed. When a sampling takes several minutes to take and transmit, this can be an exasperating experience for both the patient and the health care provider. This is particularly true since many of the patients using such devices are elderly and are intimated or confused by the monitoring procedure and equipment. Thus, it would be advantageous to provide a device that allows the patient and technician to talk to each other as the reading occurs in order to minimize errors and save time.

The prior art discloses an apparatus and a method for concurrent communication of medical patient data and voice (Saltzstein, U.S. Pat. No. 5,704,364). However, such an apparatus is expensive and complex for it requires the patient to have a life signs monitor, a digital simultaneous voice and data (DSVD) device, and a modem. Furthermore, the receiving party must also have a DSVD device and a modem. Both the apparatus and method are complex for they involve multiple series of digitizing, undigitizing, modulating, and demodulating.

Therefore, what is needed is an inexpensive and simple telephone device that allows a patient to conduct self-readings while simultaneously being able to talk and hear. A telephone apparatus with less devices and components will simplify the process of taking self-measurements as well as lower the cost of manufacturing such an apparatus.

What is also needed is a method for simultaneously transmitting biomedical readings and human voice over a telephone.

BRIEF SUMMARY OF THE INVENTION

The invention is an apparatus for simultaneously transmitting biomedical readings and human voice over a conventional telephone line. The apparatus comprises one or more sensors, a cable, and a transmitter device. In the case of an EKG signal, the sensor comprises one or more electrodes to take biomedical readings, a wire connected to each electrode, and a pad. The electrodes are disposed on the pad in a predetermined configuration so that the relative placement of the electrodes is fixed by their fixation in the pad and need not be individually placed by the patient as is the case with separate prior art EKG electrode. The wires transmit the biomedical readings from the electrodes. The cable groups the wires into a single unit and leads them to the transmitter device.

The transmitter device comprises a converter to convert the biomedical readings into acoustic signals and a transmitter speaker to emit the acoustic signals. The acoustic signals are translatable back to electrical biomedical signals by a receiving unit. The transmitter device is disposed within acoustic range of, or adjacent to the telephone microphone such that the transmitter speaker inputs acoustic signals into the telephone microphone. The transmitter device is disposed such that the telephone microphone is also available for oral speech being simultaneously transmitted into the telephone microphone with the acoustic signals converted from the biomedical readings.

The apparatus may be applied to various phone members such as a speakerphone, a conventional phone with a handset, and a headset. The apparatus may also be applied to a wireless phone such as wireless handsets and headsets wherein the telephone microphone and the telephone speaker are disposed in the wireless phone.

The apparatus may take a variety of biomedical readings, including but not limited to cardiograms, pacemaker readings, respiratory rate, heart rate, impedance for tidal volume and minute ventilation, EEG, defibrillator data output from an RF couple, data from event recorders and loop recorders, as well as other medical equipment such as IV infusion pumps and more. Furthermore, the readings may include any digital signal which is converted to analog for transmission to a receiving station.

The invention may also be characterized as a telephone line with a first end and a second end. The first end hosts the transmitter device while the second end hosts the receiving party. The apparatus is adapted to transmit oral communication from the receiving party at the second end back to the first end while simultaneously transmitting oral speech and acoustic signals from the first end to the second end.

The invention may also include its own telephone. The telephone has a microphone and a speaker. The telephone may be a handset, headset, or speakerphone. To use the telephone of the invention, the conventional handset or telephone is unplugged from the conventional telephone base. The telephone is then plugged into the conventional telephone base. The telephone may also be wireless, in which case, the telephone would not be plugged into an conventional telephone base. The wireless telephone must be configured to operate in conjunction with an conventional telephone line.

The invention may also be characterized as a method. The method comprises taking electronic measurements of biomedical data, converting the electronic measurements into an acoustic signal, transmitting the acoustic signal to the microphone, and orally transmitting human voice to the microphone simultaneously with the transmitting of the acoustic signal.

The method further comprises simultaneously receiving an incoming acoustic signal from the speaker while simultaneously transmitting human voice and the acoustic signal.

Therefore, in summary it can be appreciated that the invention makes it possible for a patient to orally communicate with the receiving party or health care provider while transmitting biomedical readings. Both the patient and the receiving party may talk and listen while biomedical readings are simultaneously being transmitted.

The invention now having been briefly summarized, it may be better visualized by turning to the following drawings wherein like elements are referenced by like numerals.

BRIEF DESCRIPTION OF THE DRAWINGS

FIG. 9 is a schematic view of the second preferred embodiment of the present invention and an conventional telephone.

The invention and its various embodiments can now be better understood by turning to the following detailed description wherein an illustrated preferred embodiments is described. It is to be expressly understood that the illustrated embodiment is set forth as an example and not by way of a limitation to the invention as defined in the following claims.

DETAILED DESCRIPTION OF THE PREFERRED EMBODIMENTS

The present invention is an apparatus for simultaneously transmitting biomedical readings and human voice over a telephone. The invention is also a telephone system adapted to receive communication from the receiving party at a second end of the line while simultaneously transmitting biomedical readings and human voice from the first end. The apparatus comprises a sensor, a cable, and a transmitter device. The sensor comprises electrodes attached to a pad with a wire connected to each electrode. The cable groups the wires into a single unit and leads them to the transmitter device. The transmitter device comprises a converter and a transmitter speaker. In operation, the sensor takes biomedical readings in the form of electronic data. The data is conveyed via the wires where it reaches the converter. The converter converts the biomedical electronic data into acoustic signal, which is emitted by the transmitter speaker in circuit with the converter. The acoustic signals are translatable back to biomedical readings by the receiving party. The transmitter speaker is disposed within acoustic range of, or adjacent to the microphone of a telephone. The transmitter speaker is disposed in such a manner as to allow oral communication from the patient to be transmitted simultaneously with the transmission of the biomedical acoustic signals. The invention may also comprise its own telephone components which may then be plugged into an conventional telephone base.

Figure 1:
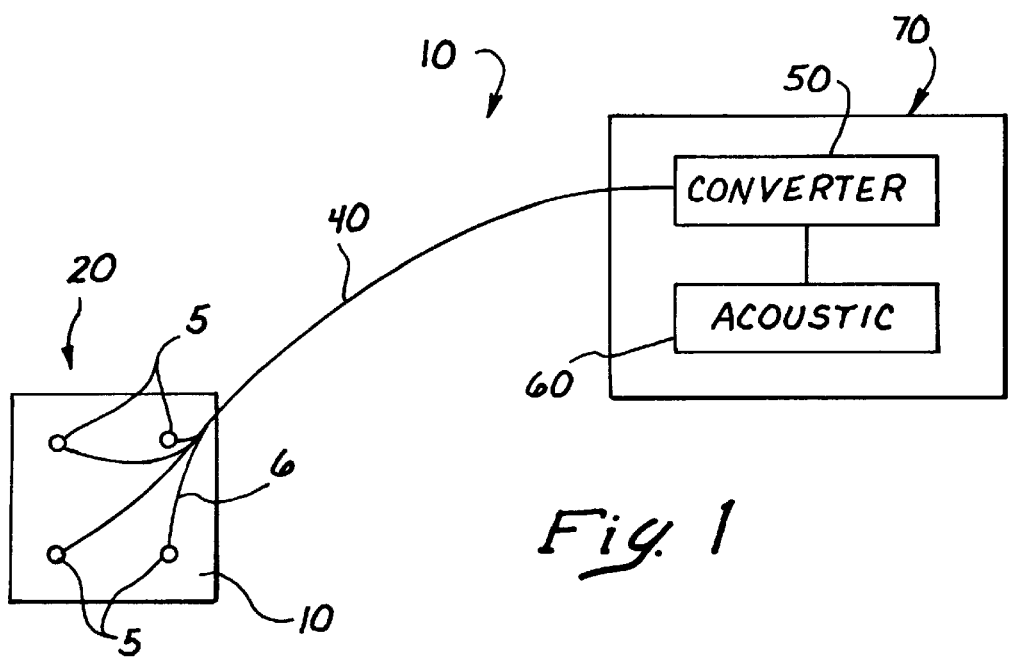
FIG. 1 is a schematic diagram of a first preferred embodiment of the present invention.

FIG. 1 is a schematic diagram of a first preferred embodiment of the present invention. The first preferred embodiment of the invention, an apparatus, generally denoted by reference numeral 10, comprises sensor 20, cable 40, and transmitter device 70. Sensor 20 comprises a plurality of electrodes 5 disposed on pad 10. Pad 10 is preferably an electrical skin pad which may attach directly onto human skin having a construction well known in the field of EKG skin electrode. Electrodes 5 are fixed to pad 10 in a predetermined configuration to obtain a desired EKG signal, thereby relieving the patient from having to determine their proper relative placement.

Each electrode 5 is connected to a wire 6. Wires 6 are grouped into a single unit by a single cable 40. Cable 40 leads to transmitter device 70. Transmitter device 70 comprises converter 50 and transmitter speaker unit 60. Converter 50 and transmitter 60 may be integral with each other, and, thus, packaged as a single unit. Alternatively, converter 50 and speaker unit 60 may be separate from each other and packaged as two separate units. Converter 50 receives, amplifies, encodes and conditions the skin EKG signals from electrodes 5 for input into speaker unit 60. The design and signal processing utilized by converter 50 is conventional. Any conversion methodology or means now known or later devised may be employed or substituted. Speaker unit 60 converts the electrical signals from converter 50, and converts them into acoustic signals in an appropriate frequency range for transmission over a conventional telephone line. Again the design and signal processing utilized by speaker unit 60 is conventional and will not be further described except where necessary to provide a contextual foundation. Transmitter device 70 may in fact be very similar to or the same of EKG transmitting units already in use.

Figure 2:
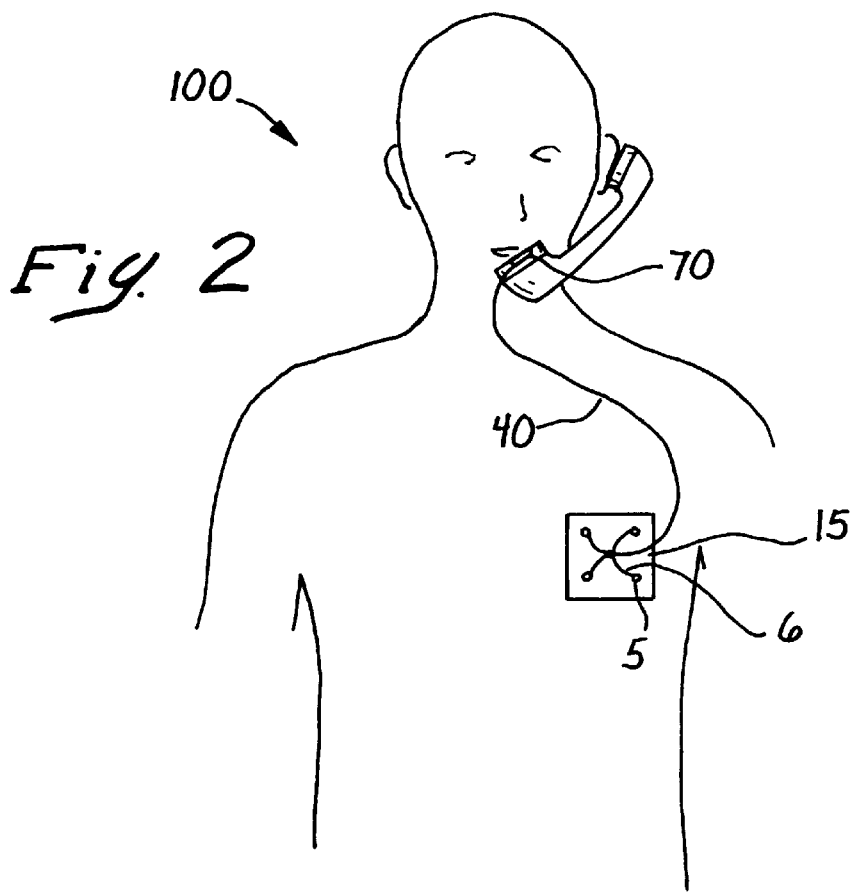
FIG. 2 is an illustrated view of the first preferred embodiment of the invention as applied to a patient.

Turn now to the operation of apparatus 10 by referring to FIG. 2. FIG. 2 is a perspective view of the first preferred embodiment of the invention 10 as applied to a patient 100. Sensor 20 is applied to the front chest wall of patient 100 by attaching pad 10 to the skin of patient 100 where biomedical readings are desired. This procedure is usually performed by the patient following the instructions of the remote health care provider who is taken the EKG reading at the other end of the phone line. Electrodes 5 are of a conventional type and comprise those well known in the art. Once pad 10 is applied to the skin of patient 100, biomedical readings are taken in the form of electronic data. Biomedical readings may comprise electrocardiograms, pacemaker readings, respiratory rate, heart rate, impedance for tidal volume and minute ventilation, EEG, defibrillator data output from an RF couple, data from event recorders and loop recorders, as well as other medical equipment such as IV infusion pumps and more. Furthermore, the readings may include any digital signal which is converted to analog for transmission to a receiving station.

Figure 3:
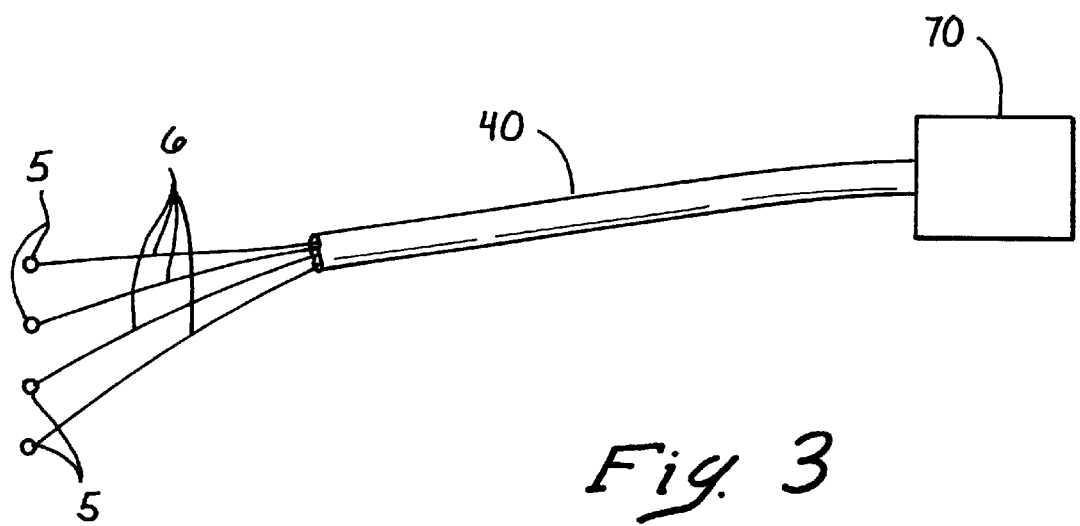
FIG. 3 is a perspective view of a cable grouping the wires from the electrodes and leading them to the transmitter device.

FIG. 3 is a perspective view of cable 40 grouping wires 6 from electrodes 5 and leading them to transmitter device 70. In FIG. 3, the electronic data is conveyed via wires 6. Cable 40 groups wires 6 into a single unit and insulate wires 6 as they travel to transmitter device 70. Cable 40 may be a variety of lengths and sizes.

Figure 4:
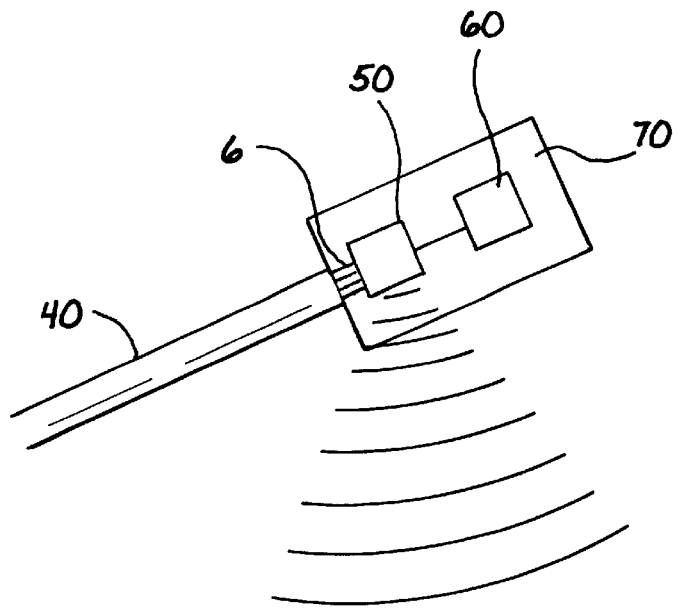
FIG. 4 is a block diagram of the transmitter device of the present invention being within acoustic range of a telephone microphone.

FIG. 4 is a schematic view of transmitter device 70 which has been place within acoustic range of telephone microphone 82. The electronic data will travel through cable 40 until it reaches transmitter device 70. Upon reaching transmitter device 70, converter 50 will convert the electronic data into acoustic signals that are emitted by transmitter speaker unit 60 in circuit with converter 50. Transmitter speaker unit 60 will emit acoustic signals which are translatable back to biomedical readings by a receiving unit on the other end of the telephone line. These acoustic signals, depicted by sound waves in FIG. 4, are received by telephone microphone 82 and are generated at a volume loud enough to allow acoustic coupling to speakerphone 82 at a reasonable distance from speaker unit 60. If speaker unit 60 is too far from telephone microphone 82, the sounds received by telephone microphone 82 will be faint and, thus, the receiving party will not be able to reliably reconvert the sounds back to biomedical readings. Transmitter device 70 is disposed such that telephone microphone 82 is also available for oral speech being simultaneously transmitted by patient 100 into telephone microphone 82 with the acoustic signals converted from the biomedical readings.

Figure 5:
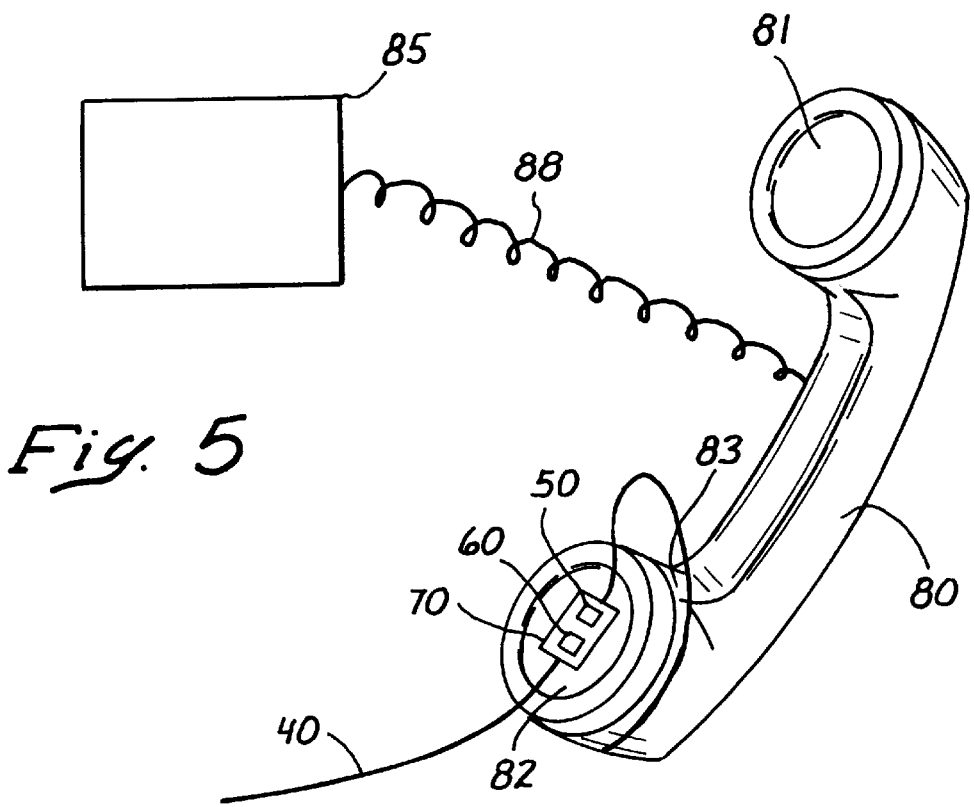
FIG. 5 is an illustrated view of the transmitter device as applied to a conventional telephone handset.

FIG. 5 is a diagrammatic view of transmitter device 70 as applied to an conventional telephone handset 80. Telephone handset 80 is connected to conventional telephone base 85 by telephone wire 88. Transmitter device 70 should preferably be small enough to be conveniently disposed within acoustic range of telephone microphone 82. In the first preferred embodiment, transmitter device 70 is disposed immediately adjacent to telephone microphone 82. Transmitter device 70 may be attached to telephone handset 80 by clip 83 or may be contained in an elastic holder (not shown) which elastically slips onto telephone microphone 82. Though a resilient clip is shown in the first embodiment of the invention, any other type of attachments now known or later devised may be used without departing from the spirit and scope of the present invention. Any attachment which leaves at least a part of telephone microphone 82 also available for conventional oral communication may be substituted.

Figure 6:
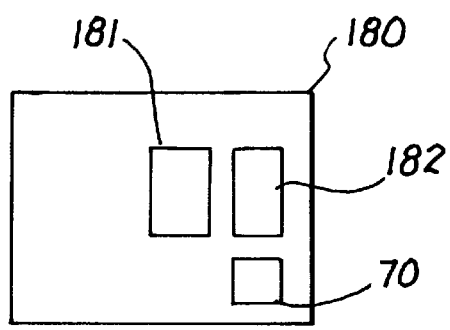
FIG. 6 is a block diagram of the transmitter device as applied to an conventional speakerphone.

FIG. 6 is block diagram of transmitter device 70 as applied to an conventional speakerphone 180 including within a housing a telephone microphone 182 and telephone speaker 181. Transmitter device 70 is disposed within acoustic range of speakerphone 180, thus allowing the patient (not shown) to have his or her hands free to move about and make any necessary adjustments while conversing with the technician.

Figure 7:
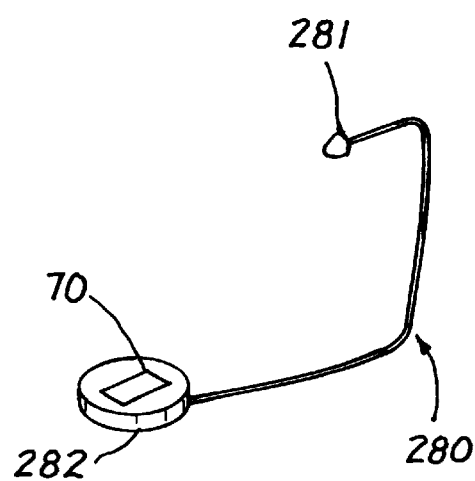
FIG. 7 is a block diagram of the transmitter device as applied to an conventional telephone headset.

FIG. 7 is a diagrammatic view of transmitter device 70 as applied to an conventional telephone headset 280, having a headset speaker 281 and a headset microphone 282. Transmitter device is disposed within acoustic range of, or adjacent to, headset microphone 282. Similar to speakerphone 180, applying transmitter device 70 to headset 280 also frees the patient to use both of his or her hands to make necessary adjustments while conversing with the technician.

Figure 8:
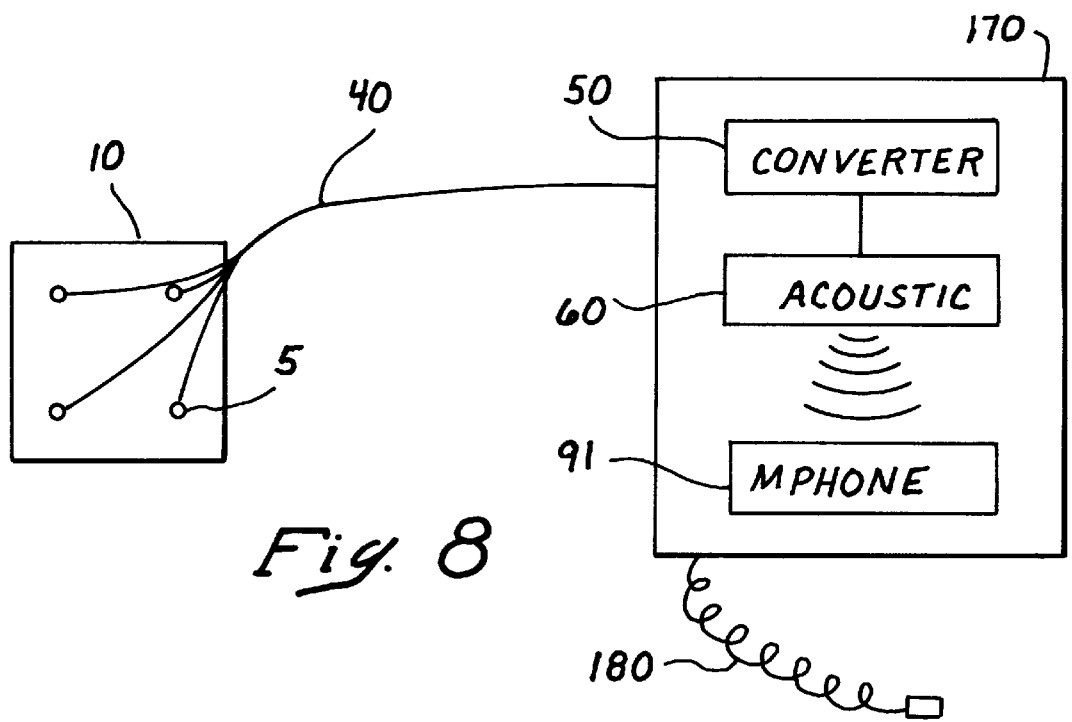
FIG. 8 is a block diagram of a second preferred embodiment of the present invention.

FIG. 8 is a block diagram of a second preferred embodiment of the present invention. In FIG. 8 transmitter device 170 comprises converter 50, transmitter speaker unit 60, and its own telephone microphone 91 which is also available for use by the patient. Thus, transmitter device 170 may be packaged as a single unit.

FIG. 9 is a schematic view of the second preferred embodiment of the present invention and a conventional telephone 86. Thus, in FIG. 9, the present invention may include its own telephone handset 200 which includes telephone speaker 92 and telephone microphone 91 as well as transmitting device 170. Transmitting device 170 includes converter 50, transmitter speaker unit 60 in operative acoustic communication with telephone microphone 91 in the mouthpiece of handset 200 similar to that shown in FIG. 8. Thus, a patient can merely unplug a conventional handset 80 from a conventional telephone base 85 at home or in the office, and plug line 180 of telephone handset 200 into telephone base 85. Telephone handset 200 may also be wireless, in which case, the telephone member 200 would not be plugged into an conventional telephone base. Similarly, a wireless headset similarly configured could be used in place of telephone handset 200.

Figure 10:
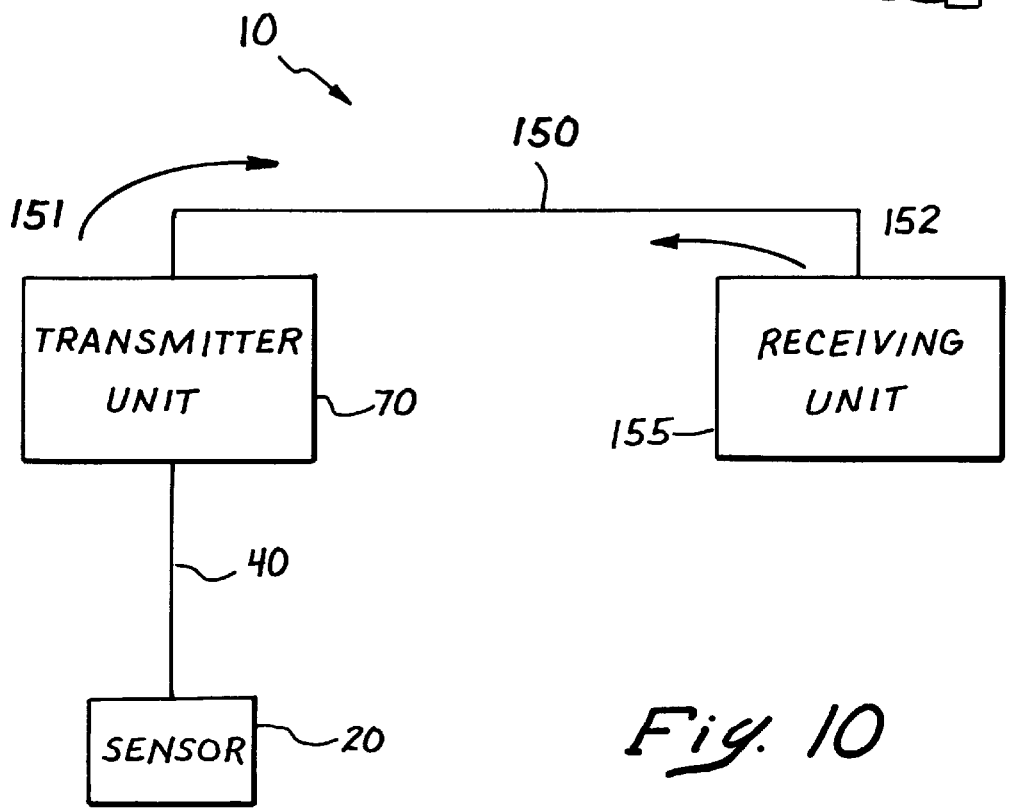
FIG. 10 is a block diagram view of the invention as a telephone line.

FIG. 10 is a block diagram of the present invention as a telephone system 10. System 10 comprises a telephone connection 150 through wires, telephone switches, phone exchanges and the like with a first end 151 and a second end 152. First end 151 of telephone line 150 hosts transmitter device 70, cable 40, and sensor 20. Second end 152 hosts receiving unit 155. Thus, invention 10 is adapted to transmit oral communication from receiving unit 155 at second end 152 back to first end 151 while simultaneously transmitting voice and acoustic signals from first end 151 to second end 152. Receiving unit 155 includes conventional circuits for receiving the acoustic signal over the line, converting it to electrical signals and printing an EKG chart or another type of medical record for diagnostic study. The receiving party may also communicate with patient 100 through receiving unit 155 during the transmission of biomedical data. Although it is anticipated that anyone simultaneously speaking on the line while biomedical data is being transmitted will corrupt the biomedical data so that a false reading is obtained, this is tolerated since such speech will occur only if the data is initially bad. In other words, the patient and technician will be speaking over the line on top of the acoustic signals representing the biomedical data to communicate that the data is erroneous and to provide instructions to readjust sensors 5 or other controls at the patient's or technician's end of the line to obtain valid data. The corrupted biomedical data will be discarded in any case.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention. Where an element is referred to in the singular form, the claims are to be understood as including the plural form. Where an element is referred to in the plural form, the claims are to be understood as including the singular form.

Furthermore, the claims are to be understood as comprising embodiments beyond what is described in this specification. This applies particularly to the method claims wherein countless varieties of structural elements may read upon those claims.

We claim:

1. An apparatus for simultaneously transmitting biomedical readings from a patient and for bidirectionally communicating voice signals over a telephone, the telephone having a telephone microphone and a telephone speaker, the apparatus comprising:
   a sensor to sense the biomedical readings; and
   a transmitter device comprising a converter to convert the biomedical readings into electrical drive signals and an acoustic circuit to convert the electrical drive signals into acoustic signals, the acoustic signals being translatable back to signals representative of the biomedical readings by a remote receiving unit, the transmitter device being disposed within acoustic range of the telephone microphone such that the acoustic circuit transmits the acoustic signals to the telephone microphone, the transmitter device being disposed such that the telephone microphone is also simultaneously available to receive oral communication from the patient simultaneously with the acoustic signals converted from the biomedical readings, the telephone speaker being disposed to be available to produce audible voice signals to the patient while the acoustic signals converted from the biomedical readings are being transmitted.

2. The apparatus of claim 1 wherein the telephone comprises a speakerphone, the telephone microphone and the telephone speaker being disposed in the speakerphone.

3. The apparatus of claim 1 wherein the telephone comprises a wireless telephone unit, the wireless unit comprising the telephone microphone and the telephone speaker.

4. The apparatus of claim 1 wherein the telephone comprises a telephone headset.

5. The apparatus of claim 1 wherein the transmitter device is temporarily disposed adjacent to the telephone microphone.

6. The apparatus of claim 1 wherein the biomedical readings comprise electrocardiographic signals.

7. The apparatus of claim 1 wherein the biomedical readings comprise a pacemaker signal.

8. The apparatus of claim 1 wherein the biomedical readings comprise at least one biomedical reading from the group including respiratory rate, heart rate, impedance for tidal volume and minute ventilation, defibrillator data output from an RF couple, data from event recorders, data from loop recorders, or signals from an IV infusion pump.

9. The apparatus of claim 1 wherein the biomedical readings comprise any digital signal being converted to analog for transmission to the remote receiving unit.

10. An apparatus for simultaneously transmitting biomedical readings and human voice over a telephone, the telephone having a handset with a handset speaker and a handset microphone, the apparatus comprising:
    a sensor having at least one electrode to take the biomedical readings, a wire coupled to each electrode, and a pad, the electrode being disposed on the skin pad in a predetermined relative pattern with respect to each other where the pad carries multiple electrodes;
    a cable grouping the wires into a single bundle where the pad carries multiple electrodes; and
    a transmitter device comprising a converter to convert the biomedical readings into acoustic signals and an acoustic circuit, the acoustic signals being translatable back to biomedical readings by a remote receiving unit, the transmitter device being disposed adjacent to the handset microphone such that the acoustic circuit inputs acoustic signals into the handset microphone, the transmitter device being disposed adjacent to the handset microphone such that the handset microphone is also available to simultaneously transmit voice signals from the patient into the handset microphone together with the acoustic signals converted from the biomedical readings, the handset speaker being disposed to provide audible voice signals from the remote receiving unit to the patient simultaneously with the transmission of biomedical readings to the remote unit.

11. The apparatus of claim 10 wherein the biomedical readings comprise electrocardiographic signals.

12. The apparatus of claim 10 wherein the biomedical readings comprise pacemaker readings.

13. The apparatus of claim 10 wherein the biomedical readings comprise at least one biomedical reading from the group including respiratory rate, heart rate, impedance for tidal volume and minute ventilation, defibrillator data output from an RF couple, data from event recorders, data from loop recorders, or signals from an IV infusion pump.

14. The apparatus of claim 10 wherein the biomedical readings comprise any digital signal being converted to analog for transmission to the remote receiving unit.

15. An apparatus for simultaneously transmitting EKG signals and human voice over a telephone system, the apparatus comprising:
    a telephone unit having a telephone microphone and a telephone speaker,
    a sensor having electrodes to take the EKG signals, a wire connected to each electrode, and a skin pad, the electrodes being disposed on the skin pad in a predetermined pattern adapted to obtain the EKG signals, the wires coupling the EKG signals from the electrodes;
    a cable grouping the wires into a single bundle; and
    a transmitter device comprising a converter to convert the EKG signals into acoustic signals and an acoustic circuit, the acoustic signals being translatable back to EKG signals by a receiving unit, the transmitter device being disposed within acoustic range of the telephone microphone such that the acoustic circuit inputs the acoustic signals into the telephone microphone, the transmitter device being disposed such that the telephone microphone is also available for voice signals being simultaneously transmitted into the telephone microphone with the acoustic signals converted from the EKG signals.

16. The apparatus of claim 15 wherein the telephone unit is a handset.

17. The apparatus of claim 15 wherein the telephone unit is a headset.

18. The apparatus of claim 15 wherein the telephone unit is a speakerphone.

19. The apparatus of claim 15 wherein the telephone system comprises a conventional handset and a conventional base unit, the telephone unit coupled to the conventional base unit in substitution for the conventional handset.

20. The apparatus of claim 19 wherein the telephone unit comprises a wireless handset.

21. A method of simultaneously transmitting biomedical signals and human voice over a telephone, the telephone having a telephone microphone and a telephone speaker, the method comprising:

sensing the biomedical data;

converting the sensed biomedical data into an acoustic signal;

transmitting the acoustic signal to the telephone microphone; and simultaneously receiving an audible voice signal from a receiving unit through the telephone speaker while transmitting of the acoustic signal.

22. The method of claim 21 wherein sensing the biomedical data senses a signal generated from an implanted pacemaker.

23. The method of claim 21 wherein sensing the biomedical data senses an EKG signal from a plurality of electrodes disposed on a skin pad which arranges the electrodes into a predetermined patterned adapted to received an EKG signal.

* * * * *